United States Patent
Eberhard

(10) Patent No.: US 10,300,192 B2
(45) Date of Patent: May 28, 2019

(54) DEVICE FOR SUPPLYING AND METERING A FLUID FOR MEDICINAL PURPOSES

(71) Applicant: B. BRAUN MELSUNGEN AG, Melsungen (DE)

(72) Inventor: Dietmar Eberhard, Kenzingen (DE)

(73) Assignee: B. BRAUN MELSUNGEN AG, Melsungen (DE)

(*) Notice: Subject to any disclaimer, the term of this patent is extended or adjusted under 35 U.S.C. 154(b) by 780 days.

(21) Appl. No.: 14/384,543

(22) PCT Filed: Nov. 6, 2012

(86) PCT No.: PCT/EP2012/071942
§ 371 (c)(1),
(2) Date: Sep. 11, 2014

(87) PCT Pub. No.: WO2013/139408
PCT Pub. Date: Sep. 26, 2013

(65) Prior Publication Data
US 2015/0032055 A1     Jan. 29, 2015

(30) Foreign Application Priority Data
Mar. 19, 2012   (DE) .................. 10 2012 102 273

(51) Int. Cl.
*A61M 5/142*     (2006.01)
*A61M 5/48*     (2006.01)
(Continued)

(52) U.S. Cl.
CPC ............ *A61M 5/142* (2013.01); *A61M 5/486* (2013.01); *A61M 5/14216* (2013.01);
(Continued)

(58) Field of Classification Search
CPC .................. A61M 5/142; A61M 5/486; A61M 2205/332; A61M 2205/3344
See application file for complete search history.

(56) References Cited

U.S. PATENT DOCUMENTS 2,274,479 A   2/1942   Inderdohnen et al.
3,178,942 A   4/1965   Bendy
(Continued)

FOREIGN PATENT DOCUMENTS

DE   30 35 703   5/1982
DE   32 09 721   9/1983
(Continued)

OTHER PUBLICATIONS

Russian Decision to Grant, with translation, for RU 2014142055/06(068083) dated Jun. 7, 2016.
(Continued)

*Primary Examiner* — Shefali D Patel
(74) *Attorney, Agent, or Firm* — RatnerPrestia

(57) ABSTRACT

A device is described for supplying and metering a fluid for medical purposes, at least comprising one pump for pumping the fluid and at least one element through which the fluid is conveyed. At least one recess is provided in the at least one element, which is tightly covered by a sensor component composed of a pressure sensitive material, wherein a material of the at least one element is harder than that of the sensor component. The device also has a force sensor with which pressure-induced changes of the sensor component in a region of the at least one recess can be measured.

2 Claims, 3 Drawing Sheets

(51) Int. Cl.
  *F04B 13/00* (2006.01)
  *F04B 19/02* (2006.01)
  *F04B 43/08* (2006.01)
  *F04B 53/16* (2006.01)

(52) U.S. Cl.
  CPC ............... *A61M 2205/332* (2013.01); *A61M 2205/3327* (2013.01); *F04B 13/00* (2013.01); *F04B 19/02* (2013.01); *F04B 43/08* (2013.01); *F04B 53/16* (2013.01); *F04B 2205/05* (2013.01); *F04B 2205/09* (2013.01)

(56) References Cited

U.S. PATENT DOCUMENTS

| | | | | |
|---|---|---|---|---|
| 3,802,265 | A | | 4/1974 | Wood |
| 4,218,926 | A | * | 8/1980 | DeVisser ............ G01L 19/0023 73/730 |
| 5,410,916 | A | * | 5/1995 | Cook ................. G01L 19/0038 600/561 |
| 5,720,721 | A | * | 2/1998 | Dumas .............. A61M 5/16854 604/118 |
| 5,951,510 | A | | 9/1999 | Barak |
| 6,171,253 | B1 | * | 1/2001 | Bullister ............. A61B 5/0215 600/486 |
| 6,523,414 | B1 | * | 2/2003 | Malmstrom ...... A61M 5/16854 73/705 |
| 6,755,079 | B1 | * | 6/2004 | Proett .................... E21B 47/00 73/152.18 |
| 7,887,308 | B2 | | 2/2011 | Navarro |
| 2008/0041474 | A1 | * | 2/2008 | Harman .................... F01N 1/12 137/808 |
| 2009/0112155 | A1 | * | 4/2009 | Zhao ................. A61M 5/14212 604/67 |
| 2011/0224603 | A1 | | 9/2011 | Richter |

FOREIGN PATENT DOCUMENTS

| | | |
|---|---|---|
| DE | 38 38 689 | 6/1990 |
| DE | 43 40 536 | 5/1995 |
| DE | 103 05 036 | 8/2004 |
| DE | 102004054606 | 8/2005 |
| DE | 10 2005 052 927 | 5/2007 |
| EP | 0 208 955 | 1/1987 |
| EP | 2 359 932 | 8/2011 |
| JP | H0562254 | 8/1993 |
| JP | 2003139635 | 5/2003 |
| JP | 2012503183 | 2/2012 |
| RU | 221 2252 | 12/2012 |

OTHER PUBLICATIONS

International Search Report for PCT/EP2012/071942 dated Jan. 22, 2013.
German Search Report for DE 10 2012 102 273.9 dated Sep. 10, 2012.
Japanese Office Action dated Aug. 30, 2016 for Japanese Application No. 2015-500781, including English translation, 8 pages.

* cited by examiner

DEVICE FOR SUPPLYING AND METERING A FLUID FOR MEDICINAL PURPOSES

CROSS REFERENCE TO RELATED APPLICATIONS

This application is the U.S. national phase application of PCT International Application No. PCT/EP2012/071942 filed Nov. 6, 2012, which claims priority to German Patent Application No. DE 10 2012 102 273.9 filed Mar. 19, 2012, the contents of each application being incorporated by reference herein.

FIELD OF THE INVENTION

The invention relates to an apparatus for supplying and metering a fluid for medical purposes, at least comprising a pump for pumping the fluid and an element through which the fluid is delivered.

BACKGROUND

Such an apparatus is in particular used in infusion or dialysis technology in order to supply a fluid and introduce it metered into a patient, wherein peristaltic pumps and syringe pumps are predominantly used in this field. Also piston pumps may advantageously be used, as U.S. Pat. No. 7,887,308 B2 for example discloses. With a piston pump it is possible to achieve a high delivery accuracy also in the case of large delivery volumes, wherein fluid is sucked in from an exchangeable storage tank.

DESCRIPTION OF THE RELATED ART

It is often desirable here to be able to integrate a pump and other components very compactly in one housing. This is the case for example when one is dealing with medical single-use articles and/or infusion technology in the field of home care, wherein pumps for exchangeable infusion containers should be easy to connect for the patient, unskilled family members or the caregiver. It has proved advantageous to accommodate the entire pump with its additional components in a type of cassette. Included among these additional components are in particular sensor systems for the detection of occlusions in order to recognize dangerous blockages or even the blockage of lines.

The detection of an occlusion takes place usually by an indirect measurement of the internal pressure in a tube which serves for supplying a fluid to a patient. If an occlusion exists, the internal pressure of the tube downstream from the pump for example increases, which can be indirectly measured. For this purpose, the tube's round cross-section deforms elliptically with a biasing force for example and the tube's internal pressure to be determined increases or reduces this biasing force which then may be determined with a force sensor. DE 38 38 689 C1 discloses exemplarily such a method for pressure measurement and occlusion detection.

When inserting a tube set in a pump, according to the current state of the art, the tube segment responsible for an occlusion sensor must additionally be inserted by hand into special supports, which can be problematic not only in the field of home care. Furthermore this method has the disadvantage that the deformation of the tube leads generally to a creep process lasting hours. This creep releases tension in the tube cross-section which leads to a continuous changing of the measured force. The undesired change in force caused by the creeping is of a similar order of magnitude to the desired measuring effect with variation of the tube inner pressure and therefore hinders the reliable recognition of an occlusion. Special elastomers such as for example silicone comprise a significantly reduced creep behavior and are therefore predestined as the tube segment for the occlusion sensor. A combination of silicon with non-silicone materials is however very costly because process-safe bonded joints are not possible.

Furthermore so-called "domes" or "pressure domes" are known in the medical technological field for the measurement of pressure. These typically comprise a measuring chamber through which a fluid flows, wherein a part of the wall of the measurement chamber is formed by a membrane which is significantly more compliant than the remaining part of the wall of the measurement chamber. Usually a measuring sensor lies on the outer side of the membrane, which records movement of the membrane with a pressure-transmitting contact. A measuring transducer then converts the pressures and pressure changes transferred via the membrane of the pressure dome into an electrical signal. For example EP 0 208 955 A2 discloses for this purpose a method for the manufacture of a pressure-transmitting contact between the membrane of a pressure dome and the pressure transmitter of a measuring transducer.

In addition DE 43 40 536 A1 discloses an apparatus for monitoring an intravenous infusion therapy whereby infusion interruptions because of a consequent increase in pressure in the infusion tube system are to be detected. Thereby a pressure transmitting capsule is inserted in the tube system, said transmitting capsule having a pressure transmitting membrane, which in turn is in contact with the membrane of a pressure sensor via a fluid-filled gap. In this way even small increases in pressure should be quickly recognized whenever the pressure transmitting membrane bends to the outside because of an increase in pressure.

Also other sensors which measure pressure changes directly at a tube through which a fluid flows are known. For example tubes may be punctually deformed by a transducer which reacts to pressure changes at the contact points, or a measuring strip is located on the periphery of the tube, which records circumference changes due to changes in the internal pressure. Furthermore DE 30 35 703 A1 for example discloses an infusion device having a pressure sensor for the recognition of occlusions, whereby the tube is clamped between a fixed and a spring loaded/elastic element such that pressure changes in the tube may be detected indirectly via the deformation of the elastic element.

SUMMARY OF THE INVENTION

All known strategies are however relatively costly or accident-sensitive and are suited only partly for a compact arrangement in a housing. An object of the invention is therefore to provide an apparatus for supplying and metering a fluid for medical purposes which permits such a compact construction and easy handling.

An apparatus according to aspects of the invention for supplying and metering a fluid for medical purposes comprises at least one pump for pumping the fluid and one element through which the fluid is pumped. At least one recess is provided in the element, which is tightly covered by a sensor component composed of a pressure sensitive material. Thereby the material of the element is harder than that of the sensor component. Furthermore the apparatus has a force sensor with which pressure-induced changes of the sensor component in the region of the recess can be measured. The invention provides an occlusion sensor in an element of a pump, through which the fluid is pumped in any case, such that a separate sensor does not have to be assembled.

The element may be for example a tubular port through which the fluid is pumped toward or away from the pump. In this case it is an inlet and/or outlet port which forms a housing for the sensor component and comprises a recess in which the sensor component is introduced. Also however the element may be a planar flange to which ports and/or cylinders for pumping the fluid are attached, wherein the fluid flows at least partially along the flange. In this case the flange forms the hard housing for the soft sensor component. Also sensor components may be introduced to a flange as well as into one or more ports.

The invention thus makes use of the operating principle of a pressure membrane, but does not use this in a separate element, rather it integrates a corresponding sensor component into an element composed of a hard material, through which a fluid is delivered anyway. Thereby the occlusion sensor's mechanical sensor component to be integrated rests on the principle of the measurement of pressure in the fluid and is realized with an elastic material which behaves physically analogously to a pressure membrane. The particular element, which is used as a housing, forms a hard component insensitive to pressure which does not deform under the occurring pressure changes. Due to the occurring deformations of the sensor component as soft component, the internal pressure in this element can on the other hand be determined.

The occlusion sensor may thus be integrated directly into a hard element so as to save space, which permits a very compact design. The element is an inlet and/or outlet port which conducts the fluid to a pump or from the same to a patient. The sensor can thus recognize occlusions ahead of and/or behind a pump. If the associated port is suitably positioned such that it can be compactly accommodated with a pump in a housing, then the occlusion sensor at this port does not require much more space. In particular the pump that is used is a volumetric pump.

The sensor component is thereby preferably an integral and non-removable part of the relevant element, such that it also does not have to be installed or even aligned during commissioning of the apparatus. This facilitates the handling of the apparatus and avoids setup errors and thus also measurement errors.

Preferably the force sensor is in contact in the region of the recess with the surface of the sensor component, wherein the force sensor comprises for example a plunger which is in direct contact in the region of the recess with the surface of the sensor component. In this way a change in the expansion of the sensor component in this region can be measured.

Preferably the sensor component is composed of an elastomer, wherein in particular it can be silicon or a thermoelastic elastomer. In this way the physical properties of this special elastomer can be advantageously used, which in particular comprises a low creep behavior. A material-fit connection of silicone and non-silicone materials is however not required since appropriate methods, such as for example injection molding methods, can be used for a sealed connection between port and sensor component. In this way the port and the sensor component may be manufactured in a two-component process. Alternatively the connection between port and sensor component may be manufactured with other connection techniques wherein for example plug-in, click, screw or adhesive joints are possible.

In a first exemplary embodiment of the invention, the sensor component is a tube which surrounds a port with form-locking fit such that it tightly covers the recess from the outside. In another exemplary embodiment this tube is attached with form-locking fit inside a port, such that the sensor component tightly seals the recess from inside. The port and the sensor component have for this purpose a similar or the same cross-section. For example a tube having a round cross-section may be introduced with form-locking fit into a round port, or may enclose the same.

Also however it can be advantageous when the sensor component has an elliptical cross-section, wherein a flat side of the sensor component is arranged in the region of the recess. This can be the case for the inner-lying as well as outer-lying sensor components, wherein the cross-section of the port must be correspondingly adjusted. With this form of soft component, the sensor component already has the elliptical deformation necessary for the internal pressure measurement, such that undesired creep behaviors with thermoplastic elastomers can be prevented already to the greatest possible extent.

The elliptical cross-section may for example be achieved by means wherein a tube having originally circular cross-section is suitably deformed before it is assembled to an inlet or outlet port. The deformation is then not brought about through the assembly, but rather there occurs a pre-deformation of the tube to the desired elliptical cross-section in order to prevent undesired creep behavior.

In another exemplary embodiment of the invention the sensor component is a specially shaped measurement membrane having a cross-section comprising at least two opposite-lying membrane sides which each are kinked inwards, while a membrane top side which connects the two membrane sides to each other is formed straight and is arranged in the region of the recess. The force sensor thus lies on a straight surface of the measurement membrane, which is no longer changed by the internal stress, such that a linear force characteristic results.

Possible areas of application of the apparatus according to aspects of the invention are (not exclusively): medical single-use articles of infusion or dialysis systems, or devices having single-use articles for the individual dosage of drugs such as in the pharmacy field. The apparatus may be integrated into a medical infusion set and thus fulfils the prerequisite for a compact cassette system for a pump-and-sensor unit. However the invention is not limited to infusion sets, rather it may be used for all medical application areas where its properties are advantageous.

BRIEF DESCRIPTION OF THE DRAWINGS

The invention is best understood from the following detailed description when read in connection with the accompanying drawings.

DETAILED DESCRIPTION OF THE PREFERRED EMBODIMENTS

Figure 1:
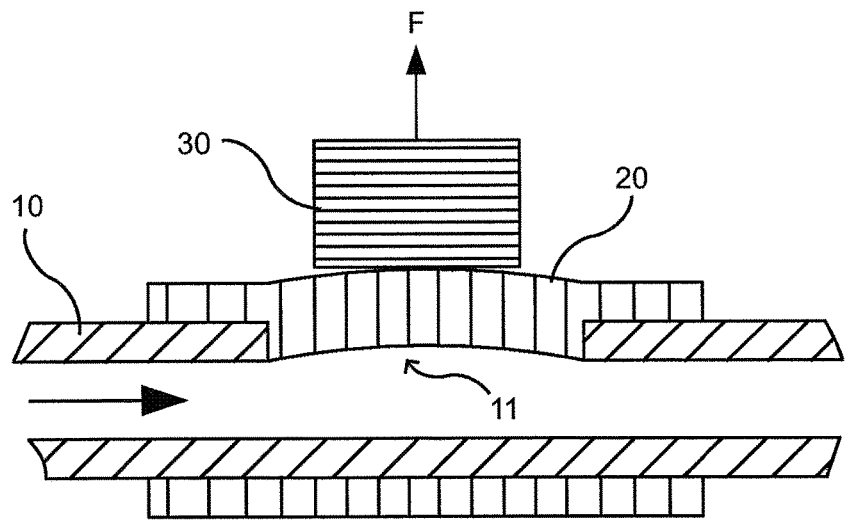
FIG. 1 shows a longitudinal section through a port having externally lying sensor component.

The longitudinal section through a port 10 shown in FIG. 1 shows an externally lying sensor component 20 which surrounds the port 10 in the region of a recess 11 with form-locking fit. A sealed connection is achieved here between the port 10 and the tubular sensor component 20. The sensor component 20 may be formed on its inner side such that it is partially inserted into the recess 11, as is shown in FIG. 1.

Figure 2:
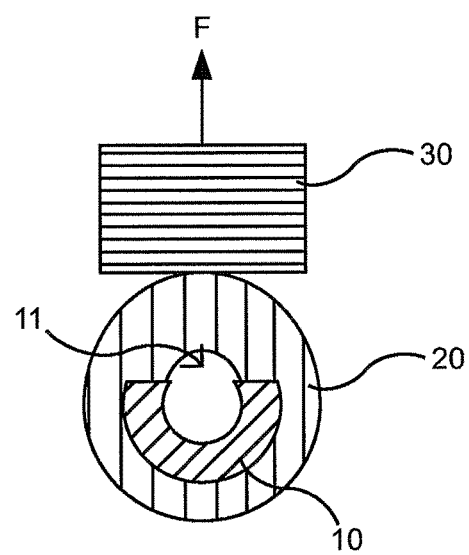
FIG. 2 shows a cross-section through a port according to FIG. 1.

The recess 11 may have an arbitrary cross-section, wherein round cross-sections have proved to be advantageous for an even force distribution. Furthermore the size of the recess 11 should be appropriately chosen. In FIG. 2 a cross-section through the middle of the longitudinal section from FIG. 1 is for example shown, whereby the recess 11 has been selected to be very deep and reaches approximately to the centerline of the port 10.

A force sensor can then reach through the recess 11 so as to establish contact in this region with the outer side of the sensor component 20. This may take place for example via a plunger 30 which bears on the sensor component. When the internal pressure in the port 10 increases due to an occlusion, the sensor component 20 bends outwardly, which can be detected by the plunger 30.

Figure 3:
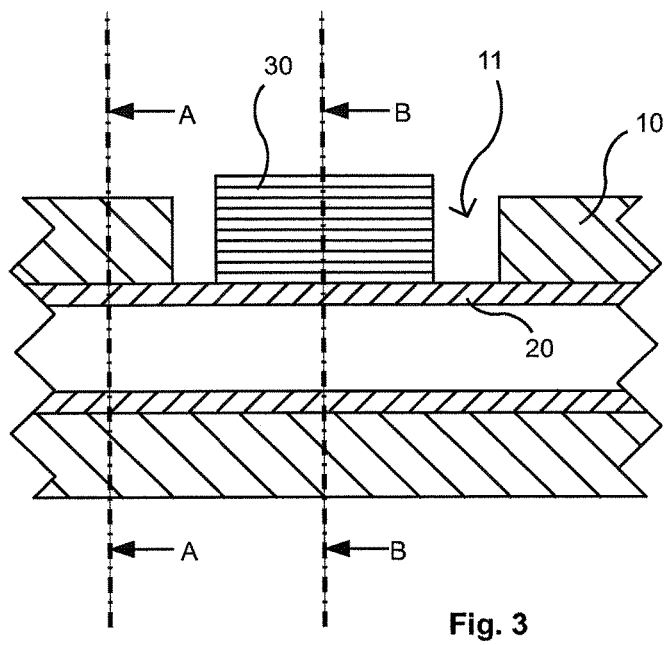
FIG. 3 shows a longitudinal section through a port having a first exemplary embodiment of an inwardly lying sensor component.

FIG. 3 shows a second exemplary embodiment of the invention, whereby a tubular sensor component 20 is attached inside a port 10 and thus tightly covers a recess 11 from inside. The plunger 30 of a force sensor can then contact the sensor component 20 through the recess 11. Thereby the inner surface of the port 10 may be configured such that it keeps the tube 20 in its position and prevents an axial sliding (not shown).

Figure 4:
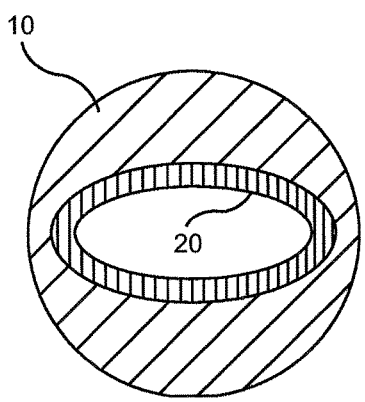
FIG. 4 shows a first a cross-section through a port according to FIG. 3.
Figure 5:
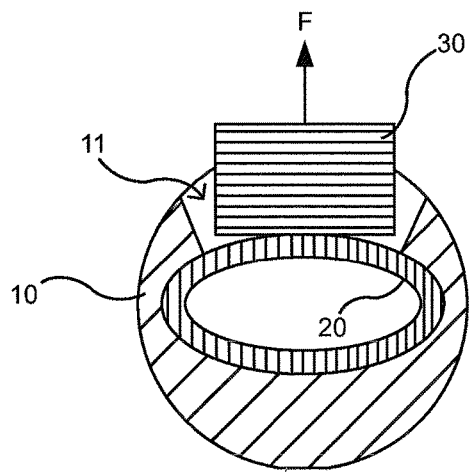
FIG. 5 shows a second a cross-section through a port according to FIG. 3.

FIG. 4 Shows a first a cross-section through such a port along line A-A, whereby it can be seen that the sensor component 20 has an elliptical cross-section. The inner wall of the port 10 is suitably formed in order to be able to accommodate the sensor component 20 with form-locking fit. A second cross-section along the line B-B is depicted in FIG. 5 and shows the plunger 30 which contacts the outer surface of the sensor component 20 through the recess 11.

Figure 6:
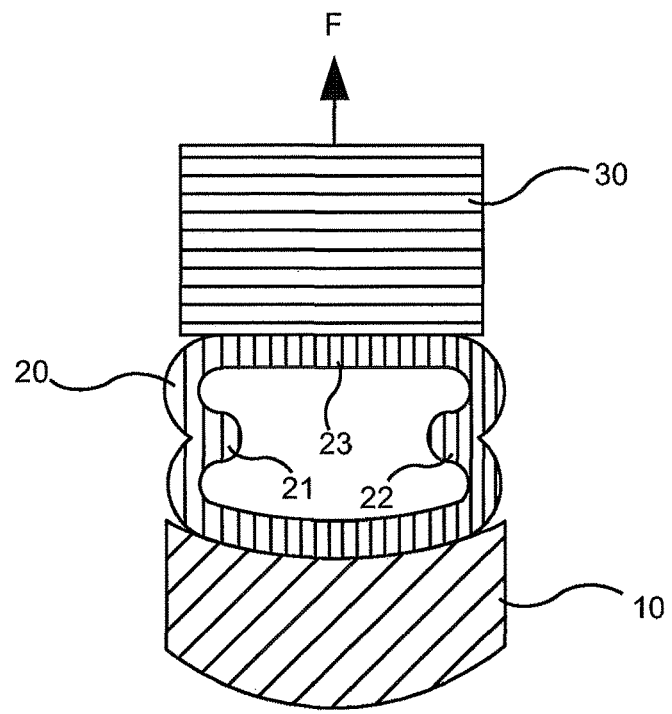
FIG. 6 shows a cross-section through a port having a second exemplary embodiment of an inwardly lying sensor component.

In order to prevent to the greatest possible extent internal stresses of the sensor component 20, this also may be configured as a specially formed measurement membrane, as is shown for example in FIG. 6. The measurement membrane 20 here comprises two opposite-lying membrane sides 21 and 22, which are kinked inwards. The membrane top side 23, which connects the two membrane sides 21, 22, is executed in a straight manner and is in contact with the plunger 30. The membrane top side 23 is no longer changed by the internal stress, which results in a linear force characteristic: force=internal pressure ×membrane surface area.

The cross-section of the sensor component 20 is thus individually formed and contains at least one of the following functional components:

A straight or approximately straight line which determines the geometry of the membrane required for measurement purposes.

A straight or curved line opposite the membrane, which performs a support function of the soft component with respect to the tubular or skeletal hard component.

A geometry for the realization of a spring function on the two sides of the soft component, so that a preload can be set up, which is necessary for the measurement of pressures below ambient atmospheric pressure. In addition the spring function is necessary such that the membrane may remove itself from its opposite-lying support surface upon an increasing inner pressure.

The inner surface of the port 10 may then be suitably executed such that the measurement membrane 20 bears on it with form-locking fit and does not extend in undesired directions, e.g. to the side, upon a pressure rise. Also this special shape of the port 10 may be provided only in the region of the occlusion sensor, whereby costly forms within the entire port can be avoided.

The hard component which surrounds the plunger 30 preferably comprises a planar surface, which lies approximately underneath the plunger's upper edge. This surface serves as an abutment surface when the plunger is pushed against another surface. The plunger can then be pushed only by the amount of its overhang, whereby a constant preload for the pressure sensor is created.

Figure 7:
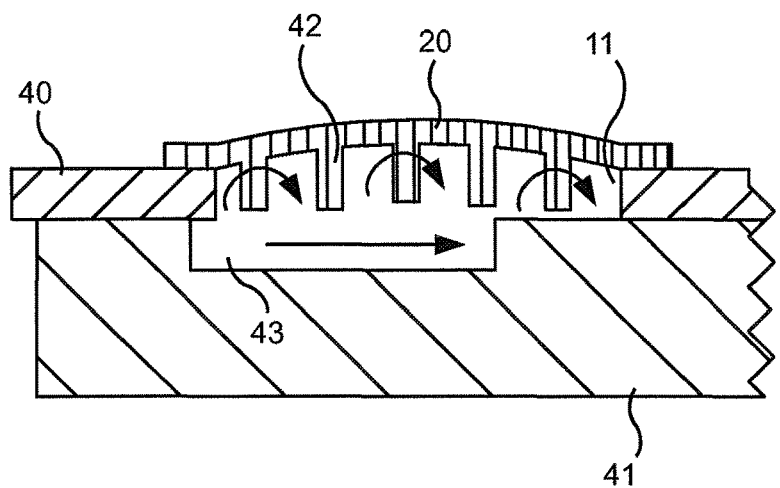
FIG. 7 shows a sensor component at a pump flange.

FIG. 7 shows an embodiment of the invention whereby the occlusion sensor is attached directly to a planar flange 40 which is part of a pump. Ports and/or cylinders of the pump may be attached to this flange 40, and a valve plate 41 may however also bear from underneath on the flange 40. Upon pumping, a fluid flows through this valve plate and thereby at least partially along the flange 40, wherein a cavity 43 is provided in the valve plate 41, through which the fluid thereby flows. A recess 11 is provided within the flange 40, which is covered by a sensor component 20. In order to be able to provide a larger surface and thereby an increased pressure sensitivity, the respective membrane of the sensor component 20 is preferably distinctly wider than the width of the cavity 43 accommodated on the valve plate 40.

The main flow of the fluid is thereby shown by a horizontal arrow to the right. However it may possible that the volume below the membrane 20 is not completely vented by this main flow. The function of the occlusion sensor is however completely provided in this case also. With an additional quantity of fluid which is required to compress the air, the response time is delayed in the case of a not completely vented volume below the membrane 20. If the membrane bottom side is provided with a single or double spiral shaped labyrinth 42, then, upon suitable configuration of the capillary effect, an additional initial flow is induced, which can bring about a most extensive venting. This initial flow is shown in FIG. 7 by several curved arrows in the clockwise direction.

The force coming from the membrane of the sensor component 20 is transferred to an external force sensor in order to recognize an occlusion (not shown). Since an occlusion in a pump feed leads to a pressure vacuum when the pump sucks, membranes 20 in the region of the pump feed must already comprise a curvature by design, which curvature then is reduced by the vacuum.

The invention claimed is:

1. An apparatus comprising:
a planar pump flange wherein:
a fluid flows at least partially along the flange,
the flange has a first surface and a second surface opposing the first surface of the flange,
the flange comprises a hard material insensitive to pressure, wherein the hard material does not deform under pressure changes, and
the flange includes a recess extending through the flange;

a valve plate bearing on the first surface of the flange, the valve plate including a cavity in fluid communication with the recess of the flange; and a sensor configured to sense occlusions via pressure changes in the fluid flowing at least partially along the flange, the sensor comprising:

a sensor component coupled to the second surface of the planar pump flange such that the sensor component has a substantially planar first side facing the cavity and a second side opposite the first side of the sensor component, the sensor component tightly covering the recess in the flange, wherein:

the sensor component is composed of a pressure sensitive material configured to deform under the pressure changes in the fluid flowing at least partially along the flange, and wherein the hard material of the flange is harder than the pressure sensitive material of the sensor component, and a spiral-shaped structure is provided on the substantially planar first side of the sensor component facing the cavity to induce an initial flow; and a force sensor in a form of a plunger in a region of the recess, wherein:

the plunger is in the region of the recess and in direct contact with a surface of the second side of the sensor component, and the plunger measures pressure-induced deformations of the sensor component caused by the pressure changes in the fluid flowing at least partially along the flange.

2. The apparatus according to claim 1, wherein the fluid flows at least partially along the flange through the cavity, and wherein the spiral-shaped structure is a labyrinth.

* * * * *